US010807087B2

(12) United States Patent
Mäkinen et al.

(10) Patent No.: US 10,807,087 B2
(45) Date of Patent: Oct. 20, 2020

(54) LATERAL FLOW DEVICE, ASSAY DEVICE AND KIT AND METHOD FOR ANALYZING A FLUID SAMPLE

(71) Applicant: Teknologian tutkimuskeskus VTT Oy, Espoo (FI)

(72) Inventors: Jukka-Tapani Mäkinen, Espoo (FI); Sanna Uusitalo, Espoo (FI); Marika Kurkinen, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 28 days.

(21) Appl. No.: 15/555,087

(22) PCT Filed: Apr. 13, 2016

(86) PCT No.: PCT/FI2016/050242
§ 371 (c)(1),
(2) Date: Sep. 1, 2017

(87) PCT Pub. No.: WO2016/166415
PCT Pub. Date: Oct. 20, 2016

(65) Prior Publication Data
US 2018/0045723 A1 Feb. 15, 2018

(30) Foreign Application Priority Data
Apr. 13, 2015 (FI) .................... 20155269

(51) Int. Cl.
*B01L 3/00* (2006.01)
*G01N 33/558* (2006.01)
(Continued)

(52) U.S. Cl.
CPC ............. *B01L 3/502* (2013.01); *B01L 3/5023* (2013.01); *G01N 21/05* (2013.01);
(Continued)

(58) Field of Classification Search
CPC .. G01N 33/558; G01N 21/05; G01N 21/6428; G01N 33/54386; B01L 3/5023
See application file for complete search history.

(56) References Cited

U.S. PATENT DOCUMENTS

| 5,637,469 A | 6/1997 | Wilding et al. |
| 5,753,519 A * | 5/1998 | Durst .................. G01N 33/586 |
| | | 436/518 |

(Continued)

FOREIGN PATENT DOCUMENTS

| EP | 1990638 A1 | 11/2008 |
| WO | WO2005118139 A1 | 12/2005 |

(Continued)

OTHER PUBLICATIONS

Mudanyali et al: Integrated rapid-diagnostic-test reader platform on a cellphone. Lab on a Chip, vol. 12, No. 15, Jan. 1, 2012, p. 2678.
(Continued)

*Primary Examiner* — Melanie Brown
(74) *Attorney, Agent, or Firm* — Laine IP Oy

(57) ABSTRACT

The invention concerns a lateral flow device, system, kit and method for analyzing a fluid sample. The device comprises a support structure, a flow channel formed in the support structure, and an injection zone in fluidic connection with the flow channel for introducing the fluid sample into the flow channel. According to the invention the flow channel comprises at least two indicator zones at least one of which is capable of producing an optically detectable response signal when interacting with the fluid sample, and the indicator zones are arranged at least partly adjacent to each other on different sections of the flow channel. The invention allows for low-cost imaging devices, such as cameras of mobile phones to be used for making challenging lateral flow diagnostics on a variety of fields of technology.

12 Claims, 7 Drawing Sheets

(51) Int. Cl.
*G01N 21/05* (2006.01)
*G01N 21/64* (2006.01)
*G01N 33/543* (2006.01)

(52) U.S. Cl.
CPC ... *G01N 21/6428* (2013.01); *G01N 33/54386* (2013.01); *G01N 33/558* (2013.01); *B01L 2200/025* (2013.01); *B01L 2300/0654* (2013.01); *B01L 2300/0809* (2013.01); *B01L 2300/0864* (2013.01); *B01L 2400/0406* (2013.01); *G01N 2201/068* (2013.01)

(56) References Cited

U.S. PATENT DOCUMENTS

| | | | | |
|---|---|---|---|---|
| 2002/0185184 | A1* | 12/2002 | O'Connor | B01F 5/0471 137/822 |
| 2004/0121356 | A1* | 6/2004 | Yamagata | B01J 19/0046 435/6.11 |
| 2005/0009101 | A1* | 1/2005 | Blackburn | B01L 3/5027 435/7.1 |
| 2007/0020768 | A1 | 1/2007 | Rundstrom et al. | |
| 2007/0042427 | A1 | 2/2007 | Gerdes et al. | |
| 2007/0122819 | A1* | 5/2007 | Wu | B01L 3/502746 435/6.11 |
| 2010/0167318 | A1* | 7/2010 | Linder | B01L 3/502746 435/7.92 |
| 2014/0057302 | A1 | 2/2014 | Hryhorenko et al. | |
| 2014/0247340 | A1 | 9/2014 | Kauniskangas et al. | |
| 2016/0074861 | A1* | 3/2016 | Phillips | G01N 33/558 506/39 |

FOREIGN PATENT DOCUMENTS

WO WO2012131386 A1 10/2012
WO WO2013181733 A1 12/2013

OTHER PUBLICATIONS

You et al: Cell-phone-based measurement of TSH using Mie scatter optimized lateral flow assays. Biosensor and Bioelectronics, vol. 40, No. 1, Jan. 2, 2013, pp. 180-185.

* cited by examiner

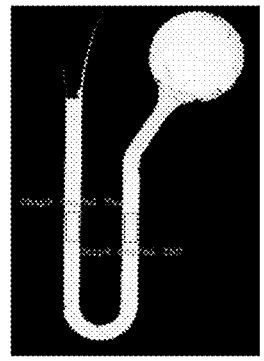
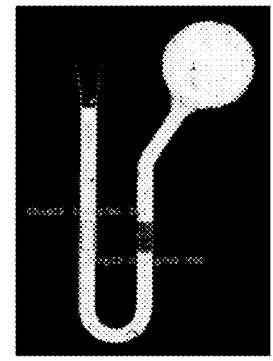
Fig. 4C                Fig. 4D
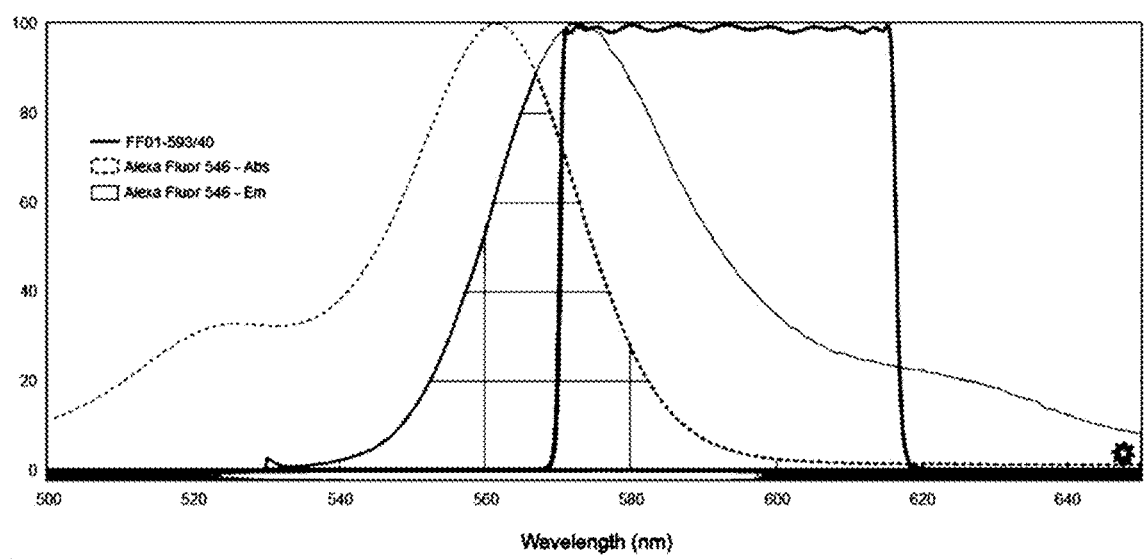
Fig. 5

LATERAL FLOW DEVICE, ASSAY DEVICE AND KIT AND METHOD FOR ANALYZING A FLUID SAMPLE

TECHNICAL FIELD

The invention relates to lateral flow assays. In particular, the invention relates to a lateral flow assay device suitable for imaging-based analysis, an imaging system utilizing such device and an analysis kit containing such device. In addition, the invention relates to a method for optically analyzing a fluid sample.

BACKGROUND ART

Biological, chemical and biochemical samples can be analyzed using lateral flow assays. Lateral flow analysis is based on injecting a fluid sample to be analyzed into a test plate, i.e. chip, comprising a flow channel provided with a substance capable of interacting with desired components of the sample and providing a measurable response due to said interaction. In optical lateral flow analyses the response is optically detectable using naked eye and/or measurable automatically using a suitable optical detector. Typically, the test plates are intended to detect the presence (or absence) of a single target analyte in sample. Such test can be used for example for medical diagnostics either for home testing, point of care testing, or laboratory use.

Camera of a modern cell phone can be utilized as the optical detector for a lateral flow assay. Such solution is disclosed for example by M. Beshay et al, *CELL PHONE-BASED LATERAL FLOW ASSAY FOR BLOOD BIO-MARKER DETECTION*, NASA Human Research Program Investigators' Workshop (2014). The solution comprises a cassette holder designed to accommodate a lateral flow test strip at a distance from a cell phone camera lens, an optical long pass filter between the lens and the test strip. The solution uses a LED of the cell phone to illuminate the sample.

There are also other mobile phone utilizing test strip reader concepts available in the market. In addition, there are dedicated lateral flow assay reading devices.

Usually, the test devices contain, in addition to a test zone with a substance capable of indicating the presence of the target analyst, a reference (control) zone which can be used for ensuring the overall operation of the test device and/or for calibrating the response. The reference zone can for example contain some second substance capable of interacting with some other substance contained in the sample matrix. An example of such test device is the home pregnancy test, which is readable by naked eye.

There are very few mobile fluorescence-based lateral flow measurement solutions available. In particular, there are no solutions, which would allow for fluorescence-based lateral flow measurements to be carried out using ordinary cell phone camera technology.

SUMMARY

It is an aim of certain embodiments of the invention to provide a novel lateral flow device and an assay device that allows for convenient analysis using mobile phone technology. A particular aim of the invention is to provide a lateral flow device that suits for mobile fluorescence measurements.

The solution is based on the idea of arranging indicator zones part of fluid channels of a microfluidic assay device side-by-side such that they can be captured to a single image easily using simple and low-cost optics.

The proposed lateral flow device comprises a support structure containing a flow channel formed therein. There is also provided an injection zone in fluidic connection with the flow channel for introducing a fluid sample into the flow channel. The flow channel comprises at least one indicator zone, which is capable of facilitating an optically detectable response signal interacting with an indicator substance. Another similar indicator zone is arranged at least partly adjacent to the first one so as to fit into an imaging area. The indicator zones may be in the same flow channel or separate flow channels formed into the support structure. Naturally, the response signal is produced using a sample with a suitable composition, corresponding to the composition of the indicator zones. Furthermore, the indicator zones are arranged at least partly adjacent to each other at different sections of the flow channel. Thus, the indicator zones are not situated directly one after another in the length direction of the channel but there may be a turn or branch, or both, in the channel between the zones. The flow channel can therefore be a single meandering channel or a branching channel network, or combination thereof, where the diagnostically relevant portions are placed within a small imaging area in a lateral direction of the device. In particular, they may be located side-by-side in a direction transverse to flow direction of a section of the channel containing one of the indicator zones.

The proposed assay device comprises a docking station having a first docking zone for an imaging device and a second docking zone for a lateral flow device containing a fluid sample to be optically analyzed using said imaging device. The first docking zone is adapted to hold a terminal device, such as a mobile phone, equipped with a camera as said imaging device and the second docking zone is adapted to hold a lateral flow device comprising at least two indicator zones arranged in different flow channel sections adjacent to each other, and at least one of the indicator zones being capable of producing an optically detectable response signal when interacting with a fluid sample provided thereto. In addition, the docking station comprises an optical unit capable of capturing said at least two indicator zones of the lateral flow device into a single image of the camera. The optical unit may include a magnifying lens allowing for the indicator zones being imaged at shorter distance from the camera than without said optical unit.

The present method of analyzing a fluid sample, comprises providing a flow channel comprising at least two indicator zones at least one of which is capable of providing an optically detectable response signal upon interaction with the fluid sample, providing the fluid sample to the flow channel such that the fluid sample flows into said at least two indicator zones, and optically detecting the response signal of said at least two indicator zones. The flow channel comprises at least two indicator zones which are arranged at least partly adjacent to each other on different portions of the flow channel, and said detecting comprises capturing said at least two indicator zones into a single digital image, for example using a camera unit of a mobile phone.

Finally, the invention provides a lateral flow assay kit comprising a lateral flow assay system and one or more lateral flow devices as described above or in more detail hereinafter.

More specifically, the invention is characterized by what is stated in the independent claims.

The invention provides considerable advantages. Most importantly, it allows for more than one indicator zones subjected to a single sample to be imaged simultaneously. Thus, it ensures that the measurement environment and adjustments are the same for all indicator zones, making their analysis reliable and comparison possible and at least more reliable compared with a situation where the zones would be imaged with different shots.

In addition, imaging can be carried out using existing and inexpensive digital cameras, such as those in mobile phones. It therefore provides a novel type of product to the lab-on-chip product family and also extends the uses of microfluidic chips to novel applications.

The imaging process is also faster than with a plurality of shots and moving of the sample between the shots.

The invention suits well for multi-analyte measurements. In this case, the different indicator zones are adapted to respond optically to different analytes.

The present lateral flow device can be manufactured using commercially available manufacturing methods. The present concept requires the channel network—or at least portion thereof containing the indicator zones—to be manufactured on small lateral area, whereby the present device is inherently small and therefore cost-effective to produce.

The invention can be used for a variety of diagnostic applications in healthcare, wellbeing, or environmental or process monitoring, to mention some examples. More specific potential application areas include immunoassays, such as drug testing, and mobile health applications.

The sample fluid can be in particular bodily fluid such as blood, serum, saliva, urine or water to mention some examples.

In summary, the invention allows for low-cost and mobile imaging devices, such as cameras of mobile phones to be used for making challenging lateral flow diagnostics on a variety of fields of technology.

The dependent claims are directed to selected embodiments of the invention.

According to one embodiment, at least two of the indicator zones are provided in the flow channel such that the fluid sample is arranged to flow into essentially opposite directions therein. This can be achieved by providing a turning portion, such as a U-shaped portion, in the flow channel, whereby the indicator zones are located at different sections of the flow channel, the sections separated by the turning portion. According to another embodiment, the flow channel is branched into two or more branches and the indicator zones are located at different branches thereof. Both solutions can be used to achieve a situation, where the indicator zones are located closer to each other when measured along a straight line than when travelling along the channel (or channel network). In particular, the indicator zones can be positioned to fit into a circular imaging area having a diameter of 5 mm, in particular 3 mm in a plane of the support structure. Thus, relatively small field-of-view device like mobile digital microscopes are able to capture the diagnostically essential portion of the device in a single shot.

According to one embodiment, the shortest distance between the indicator zones is less than 10 times, in particular less than 5 times and typically less than 3 times the width of the flow channel. With typical channel widths (1 mm or less), this ensures that the zones are relatively close to each other for single-shot imaging purposes.

According to one embodiment, at least one of the indicator zones comprises an indicator substance capable of providing an optical response signal upon interaction with matrix of the fluid sample. Likewise, at least one of the indicator zones may comprise test substance capable of providing an optical response signal upon interaction with analyte. Of particular importance in diagnostic applications is an embodiment where at least one of the indicator zones contains control antibody and at least one other indicator zone contains test antibody.

According to one embodiment, at least one of the indicator zones comprises a fluorophore, i.e., substance capable of providing a fluorescent response signal upon interaction with at least one of the (expected) components of the fluid sample.

According to one embodiment, the support structure is transparent on at least one side, in particular the top or bottom side of a plate-form structure, at least in the region of the indicator zones so as to allow optical imaging thereof after the sample has been entered.

The support structure can comprise a planar plate comprising a uniform bottom section, at least partly transparent top section comprising said injection zone, and an intermediate section between the bottom and top section, the intermediate section being patterned to define the flow channel in the lateral dimension of the plate.

The location of the imaging area and/or the indicator zones can be marked on the plate using visually detectable markers.

As concerns the docking station according to the invention, the optical unit provided therein may comprise a light source for illumination of the indicator zones of the lateral flow device. There may also be provided a bandpass filter for filtering at least part of wavelengths of the illumination light internally reflected from the conversion unit or from the lateral flow device. The optical unit of the docking station is capable of capturing, in conjunction with the mobile phone camera, the indicator zones of the lateral flow device into a single image of the camera.

The optical unit has a field of view having a diameter covering the imaging area, i.e. the indicator zones, of the lateral flow device, when placed into the second docking zone. Typically, the imaging area is not more than 10 mm or less, in particular not more than 5 mm, at a distance from the optical unit corresponding to the distance of the indicator zones from said optical unit.

According to one embodiment, the optical unit comprises a single optical lens, such as a one molded from plastic, provided with optical magnifying zone in the vicinity of its optical axis and means of guiding illumination light to the lateral flow device from a light source via a fringe zone around the magnifying zone. The illumination light may be guided to the device through the fringe zone and the refracted and/or fluorescent light collected through the magnifying zone to the camera of the mobile phone.

According to one embodiment, the system comprises a software product capable of being executed in a mobile phone adapted to be docked into the first docking zone and comprising software means for imaging the indicator zones for producing an analysis image and analyzing the analysis image for deriving a parameter descriptive of the composition of the sample using data of the analysis image at the region of both indicator zones.

Definitions

"Lateral flow assay" means an assay where the sample flow takes place at least partly parallel to a surface through which the sample and/or chemical or physical phenomena contributed by the sample can be optically imaged.

The term "indicator zone" is herein used to describe a zone in a flow channel of a lateral flow device that must be inspected to be able to derive intended results of the assay. In particular, the term refers to a zone which has diagnostic relevance in the assay concerned and can be optically inspected from outside the assay device. According to one specific embodiment, an indicator zone contains fluorophore.

"Sections" of a flow channel are channel portions, typically of constant width and/or straight shape, between other features of the device, such as injection zone or waste reservoir, and/or turns or branches of the channel.

The indicator zones being arranged "at least partly adjacent to each other at different sections of the flow channel" means that there is at least one turn (meander) and/or branch in the channel between the zones such that the zones come closer to each other than without said turn and/or branch (i.e. as if the channel was straightened between the zones). In particular, the zones can be adjacent such that one can draw an imaginary line, which is perpendicular to the direction of the flow channel within at least one of the indicator zones, such that the line intersects with the other indicator zone. That is, the zones are not situated one after along a single straight portion of the channel, like in some conventional lateral flow devices. In particular, the zones can be located partly or entirely side-by-side in a direction transverse to direction of fluid flow in the flow channel, particularly on parallel sections of the flow channel.

Next, selected embodiments of the invention and advantages thereof are discussed in more detail with reference to the attached drawings.

BRIEF DESCRIPTION OF THE DRAWINGS

FIGS. 4C and 4D show fluorescent partial images of the THC immunoassay chip according to FIG. 4A with THC concentrations of 0 and 250 ng/ml, respectively.

FIG. 5 shows a graph of absorption and emission spectra of a fluorophore and filter spectrum of a bandpass filter used in the Example.

DETAILED DESCRIPTION OF EMBODIMENTS

Lateral Flow Device

Figure 1A:
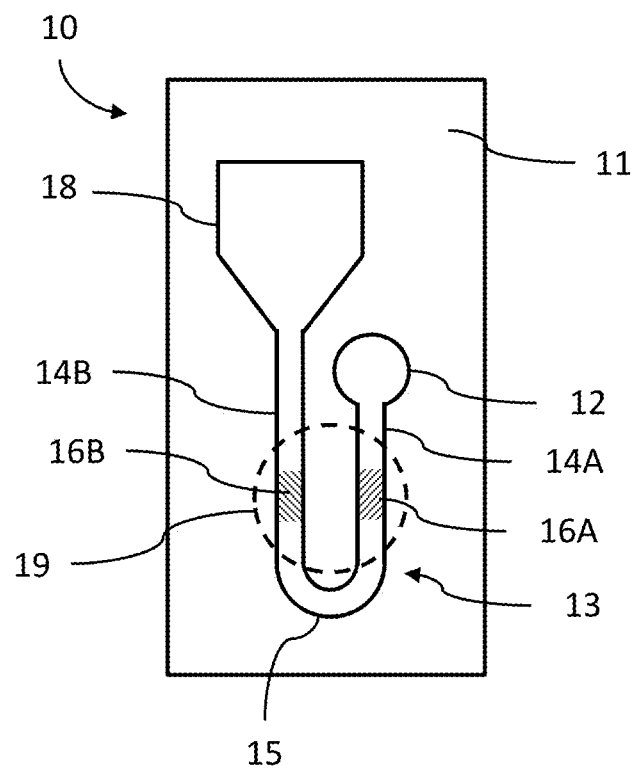
FIG. 1A shows a lateral top view of the present device according to one embodiment of the invention.
Figure 1B:
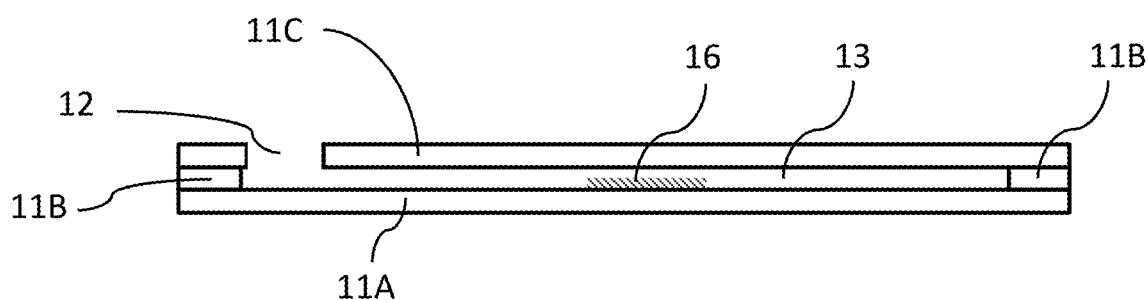
FIG. 1B shows a cross-sectional of an exemplary structure of the present device according to one embodiment.
Figure 1C:
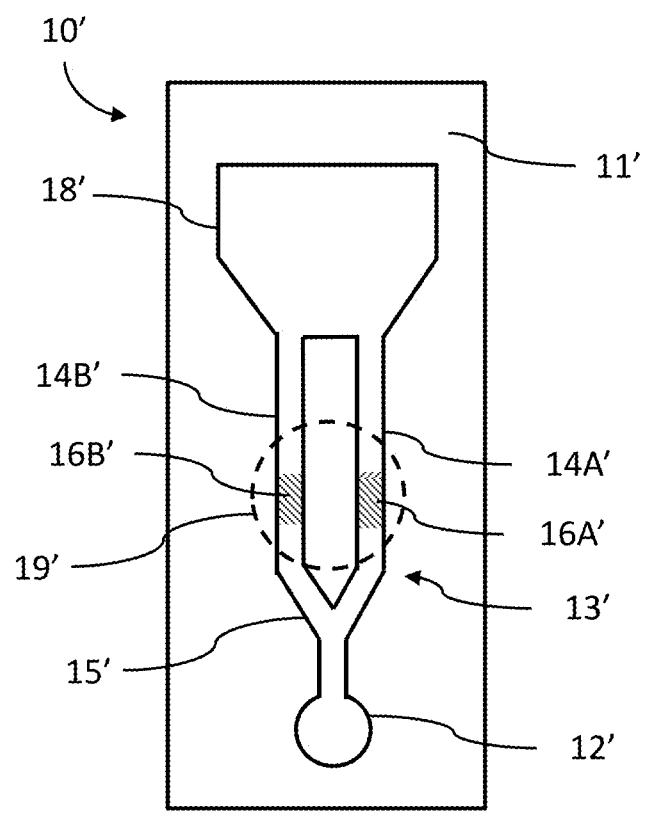
FIG. 1C illustrates a lateral flow plate 10' with a branched flow channel 13' according to an alternative embodiment.

Exemplary embodiments of the lateral flow device according to the invention are illustrated in FIGS. 1A-1C and described below. For simplicity, the illustrated embodiments contain only two indicator zones, i.e. a reference zone and an actual test zone, although configurations with more indicator zones are possible too.

FIG. 1A illustrates a lateral flow plate 10 with a meandering flow channel according to an embodiment. The plate 10 comprises a support structure 11 defining a flow channel 13. At one end of the flow channel 13, there is an injection zone 12 for providing the sample to the flow channel 13. At the other end, there is a waste reservoir 18 (suction pad), to which the portion of the sample, which has passed the whole channel 13, is collected. The channel 13 itself comprises a first portion 14A, a second portion 14B and a U-shaped turning portion 15 interconnecting the first and second portions 14A, 14B. The first and second portions 14A, 14B are arranged parallel to each other. The first portion 14A comprises a test zone 16A and the second portion 14B a reference zone 16B (or vice versa). The test and reference zones 16A, 16B are indicator zones in the flow channel 13 and may herein be referred as the first indicator zone 16A and the second indicator zone 16B. The test and reference zones 16A, 16B are aligned with each other side by side so that they fit into an imaging area 19, which is illustrated herein with a dashed line. Naturally, the imaging area 19 may have a different shape, such as quadrilateral, oval or trilateral, for example. The sample flow direction at the test and reference zones 16A, 16B are opposite.

Figure 3A:
FIG. 3A shows a photograph of a lateral flow chip manufactured.
Figure 3B:
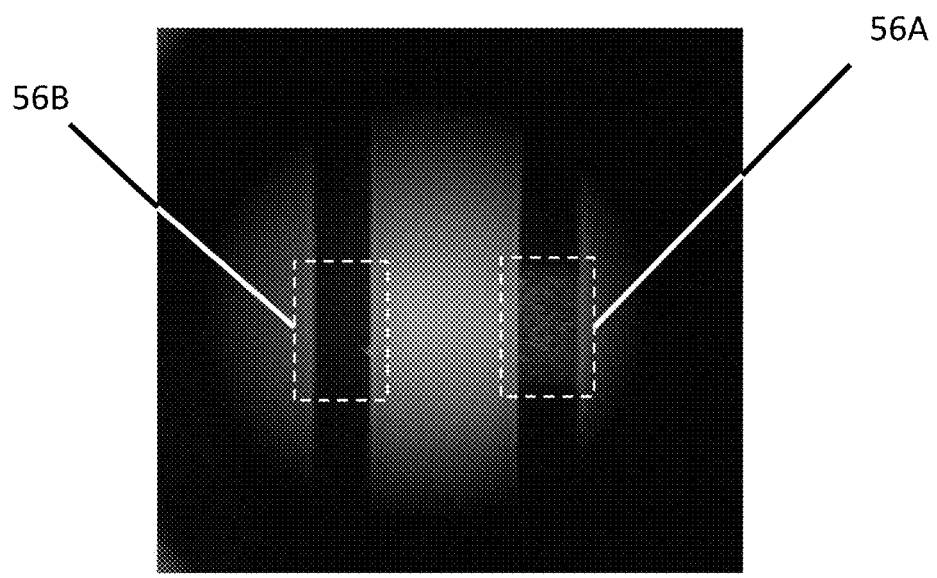
FIG. 3B shows a microscopic fluorescence image of indicator zones of the chip according to FIG. 3A, obtained using a camera of a mobile phone, microscopic adapter lens and bandpass filter.

FIG. 3A shows a real photograph of a lateral flow chip with a channel of the type described above. FIG. 3B shows the imaging area of the chip of FIG. 3A with a measurable difference in the optical response signals of the indicator zones 56A and 56B.

FIG. 1B shows an exemplary structure of the support structure of the device. The structure comprises a bottom section 11A, a top section 11C ("lid") and an intermediate section 11B between them. The intermediate section 11B defines the lateral shape of the flow channel 14. Chemical substance(s) of the test or reference zone 16 is/are arranged in the flow channel 13 so that the fluid becomes into contact therewith. The different sections 11A, 11B, 11C can be distinguishable layers stacked on top of each other but two or all three of the sections can also be manufactured from uniform material.

The width of the flow channel may be for example 0.01-2 mm and thickness for example 0.01-1 mm.

The structure can be made from plastic, glass, silicon, or a mixture thereof, to mention some examples. A plastic channel pattern can be formed for example by laser cutting, die cutting, hot pressing, extrusion molding, engraving or printing, followed by stacking of the intermediate, bottom and/or top layers, if needed. These techniques are well suitable for industrial-scale manufacturing.

According to one embodiment, the structure comprises a layer structure made at least partly from plastic, such as PMMA. There may be provided an even plastic layer as the bottom section 11A, a through-cut channel pattern containing intermediate section 11B and a plastic layer with an injection hole as the top section 11C stacked. Alternatively, the bottom and intermediate sections may be provided as a unitary plastic piece with engraved channel patterns and a plastic layer as the lid. Stacking can be achieved by gluing, taping or hot-pressing, for example. Naturally, functionally similar structures can be made from other materials too.

The flow channel 13 formed into the lateral flow plate 10 is hollow. That is to say the flow of liquid in the flow channel 13 is based on dimensioning the channel so as to excite capillary action as opposed to using a particular lateral flow matrix. Lateral flow matrixes are used in the prior art as a medium to advance flow by capillary action in a channel, which is not dimensioned to provide capillary action. The matrixes employ porous or bibulous materials, such as cellulose, paper, nylon, etc. The hollow flow channel 13, however, promotes lateral flow by appropriate dimensioning of the flow channel 13 and further promoted by a suction pad arranged to the waste reservoir 18 at an end of the flow channel 13. In other words, the flow channel 13 is flow medium free. As best seen from FIG. 1B, the flow channel 13 is being delimited by the bottom section 11A, intermediate section 11B and top section 11C without an intermediate flow matrix occupying the space there between. As a result, the lateral flow device does not need a separate enclosure for the flow channel, which is formed into the lateral flow plate 10. Accordingly, the channel is closed, which means that the top section 11C renders the flow channel 13 unexposed to the environment.

FIG. 1C illustrates a lateral flow plate 10' with a branched flow channel 13' according to an alternative embodiment. Again, there is provided a support structure 11' defining a flow channel 13'. The injection zone 12' is used for providing the sample to the flow channel 13', which contains a branching portion 15', comprising for example a Y-shaped branch. The branching portion 15' divides the channel into two branches 14A', 14B', which run in parallel towards a waste reservoir 18' at the other end of the flow channel 13'. Both branches 14A', 14B' may also have separate waste reservoirs. The first branch 14A' comprises a test zone 16A' and the second branch 14B' a reference zone 16B' (or vice versa). In this configuration too, the test and reference zones 16A', 16B' are aligned with each other side by side so that they fit into a small imaging area 19', which may be circular, for example. Sample flow direction at the test and reference zones is the same.

The flow channel or branches thereof are dimensioned such that the fluid to be used as sample flows by capillary action. In addition, the waste reservoirs 18, 18' are absorptive, i.e., designed to cause a suction force once the samples reach them. The suction empties the channel(s) at least partly.

In the illustrated configurations, the test and reference zones 16A, 16B (16A', 16B') are entirely aligned, but they can also be only partially aligned as far as both, or parts of both, fit within the imaging area 19 (19'). Moreover, the angle between channel orientations at the test and reference zones need not be 0 degrees, but the channels can be tilted with respect to each other.

In order to ensure sufficient optical signal from the indicator zones, it is proposed that they extend to at least some extent in the direction of the flow channel. According to one embodiment, the length of the zones is larger than their width, in particular at least twice the width, such as at least 0.5 mm, in particular at least 1 mm. According to another embodiment, the channel comprises a plurality of small indicator zones for forming a micro array indicator zone for enabling multi-analyte detection.

The turning portion 15 or the branching portion 15' can have an alternative shape too, as long as it interconnects the portions 14A, 14B or branches 14A' 14B' such that the test and reference zones 16A, 16B or 16A', 16B' are placed sideways close to each other. The turning portion 15 can have for example a V-shape and the branching portion a T-shape.

According to another embodiment (not shown) the first and second indicator portions are not provided as portions of the same flow channel but different ones. In particularly it is also possible to arrange two separate flow channels, namely a first and second flow channel, which comprise a first and second indicator portion, respectively. According to such an embodiment, the first and second indicator portions of the first and second flow channels are configured to appear adjacently in the imaging area, whereas the rest of the flow channels may be distant from each other. In such a case, both the first and second flow channel may comprise the necessary injection zones and waste reservoirs at opposing ends of the flow channels.

Fluorophores are optionally contained in the system. Antibodies provided with fluorophores may be e.g. printed onto the injection zone, where they are dissolved into the sample. The sample conveys the fluorophores to the indicator zones, where a sandwich comprising capture antibody, analyte and fluorescently labeled detection antibody is formed. The imaging is based on detecting fluorescent emissions of the indicators, shown at distinct wavelengths or a broader wavelength range, using a suitable optical setup, which is described in more detail below. Typically, the emission wavelength or wavelengths are higher than the excitation wavelength.

According to one embodiment, the indicator substance(s) is/are printed in the channel before stacking of the support structure, i.e., closing of the channel.

According to one embodiment, the flow channel comprises, a blood filtration membrane in front of at least one of the indicator zones.

Imaging Device

Figure 2A:
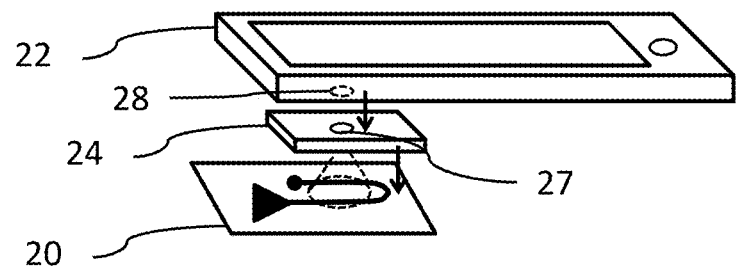
FIG. 2A illustrates a measurement setup using a mobile phone, intermediate lens and a lateral flow device of the present kind.

FIG. 2A shows the principle of an exemplary imaging device utilizing an above described lateral flow plate 20. Imaging is carried out using a camera 28 of a terminal device such as a mobile phone 22, tablet, smart watch or the like. In the following examples, the terminal device is being described as a mobile phone. Between the mobile phone 22 and the flow plate 20, there is an optical unit 24, which contains a microscopic lens 27 that makes the camera suitable for taking a sharp close-up image of the imaging area containing the indicator zones of the flow plate 20 and optionally also comprises a light source capable of illuminating the indicator zones. In general, the camera 28 and the microscopic lens 27 work together so that a large enough portion of the plate 20 can be captured to a single image. The closer together the indicator zones are on the plate, the smaller the imaging area can be.

In one embodiment, the camera 28, the optical unit 24 and the plate 20 are during imaging stacked firmly against each other such that the imaging situation is geometrically as constant as possible. According to one embodiment, the indicator zones of the plate 20 are symmetrically positioned with respect to the optical axis of the system such that they are evenly imaged.

Figure 2B:
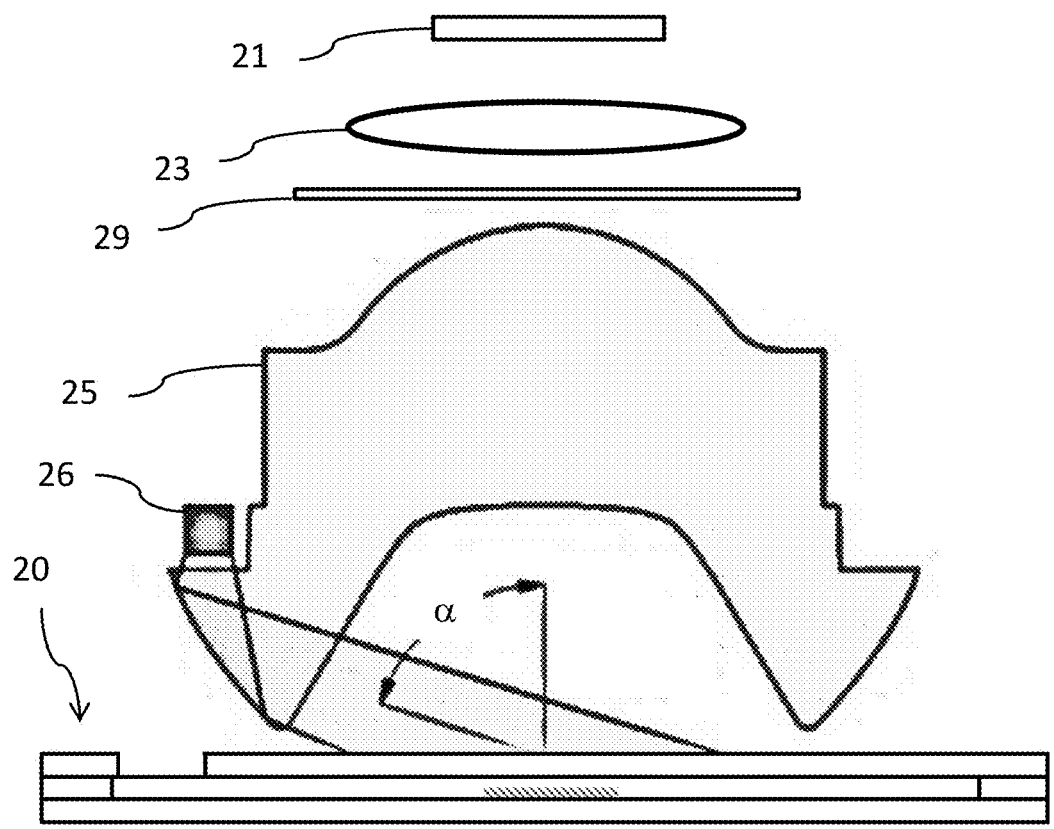
FIG. 2B shows as a cross section an exemplary optical setup according to one embodiment of the invention.

FIG. 2B shows an exemplary implementation of the optical device in more detail. There is provided an imaging panel 21, such as a CCD or CMOS panel, and imaging optics 23 of the camera 28 of the mobile phone 22. The lens of the optical unit is denoted with reference numeral 25. The lens contains a magnifying central portion, herein implemented as convex-concave lens with the convex surface facing the camera and concave surface facing the flow plate 20. There is also provided a light source 26, such a LED or laser source, whose light is directed to a fringe area of the lens 25, from which its is reflected by total internal reflection from a slanted portion of the lens 25 to the imaging area of the flow plate 20. The illumination angle at can be e.g. 45-85 degrees, in particular 60-80 degrees.

One exemplary conversion unit which is optically suitable to be used in the present invention is the KeepLoop unit provided by KeepLoop Oy, Finland.

In particular when fluorescence-based imaging is taken advantage of, there may also be provided a selective filter, such as a bandpass filter or band-reject filter, between the lens of the optical unit and the camera of the mobile phone for filtering out undesired bandwidths of light, in particular the illumination wavelength. This prevents any illumination light directly entering the imaging panel because of reflections in the lens or at the plate, for example. The filter is shown as an element 29 in FIG. 2B.

A filter is not necessarily needed in particular if a monochromatic light source is used for illumination of the plate or if the emission bandwith of the light source is otherwise narrow. It is also proposed that the plate is in this case manufactured from a low-autofluorescence material, such as glass.

It should be noted that in particular when using a dedicated reader, no imaging lenses are necessarily needed at all, but the imaging can be made using a direct image forming at the imaging sensor.

Figure 2C:
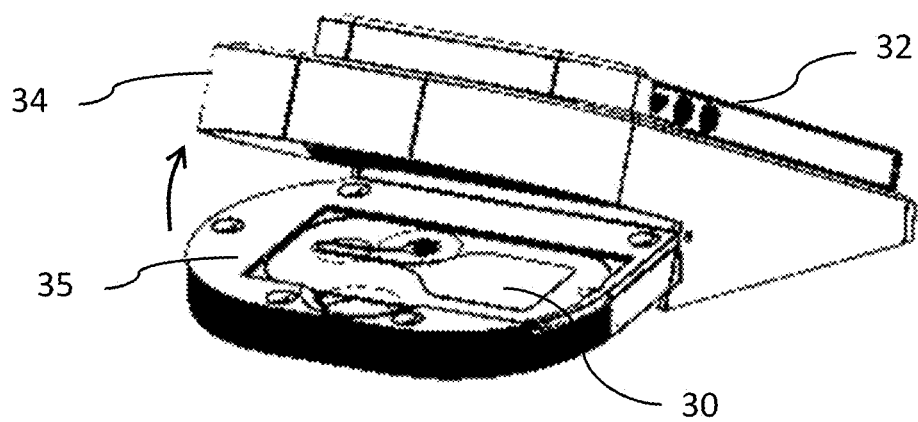
FIG. 2C shows a docking station 34 comprising on its upper surface a first docking zone for a mobile phone 32 and a second docking zone for a lateral flow plate 30.

FIG. 2C shows a docking station 34 comprising on its upper surface a first docking zone for a mobile phone 32 and a second docking zone for a lateral flow plate 30. The optical unit is positioned inside the body of the station 34 between the first and second docking zones. The first docking zone is capable of immobilizing the phone 32 such that its camera is aligned in a predefined position. In particular, there may be members holding the phone 32 laterally in a fixed position such that the camera of the phone is aligned with the optical unit built in the docking station. The second docking zone is also designed to immobilize the lateral flow plate 20 such that its imaging area is aligned with the camera and the optical unit. In the illustrated example, the second docking zone is implemented using frame 35 placed below the first docking zone and having a recess for the plate 30. The frame 35 also comprises a mechanism allowing the plate 30 to be inserted and removed conveniently. In this case, the frame 35 is hinged to the main body of the docking station 34 such that during imaging, the frame 35 is closed towards the body and during insertion and removal of the plate 20, the frame is in an opened position.

FIG. 2C shows only one example of the docking station. There are numerous other mechanical implementation options available too. For example, there may be provided a slot where the flow plate 30 can be slid.

Once the analysis image containing the two or more indicator zones has been captured, a processor of the mobile phone is used to derive a parameter depicting the composition of the sample based on pixel or subpixel (color) intensities of the analysis image using an analysis algorithm defined in a software executed in the mobile phone.

An exemplary analysis algorithm for fluorescence-based assays proceeds as follows:
1. Selecting a desired region of interest (ROI) from the analysis image, containing at least a portion of one indicator zone.
2. Forming a single-channel (image of ROI). If green (G) excitation light is used, for example, red (R) channel can be chosen to avoid excitation light from appearing (in particular if a physical filter is not used or as an additional filter).
3. Calculating a histogram of the single-channel image and from the histogram at least one of the following values
   Mean value,
   Median value,
   Mode value (most common value),
   95 percentile (depicting well the maximum intensity)
   97 percentile (depicting well the maximum intensity)
4. Comparing the value with a reference curve obtained using known concentrations of the analyte and thus obtaining an estimate for the concentration of the measured analyte.

Other non-illustrated examples of the invention include competitive immunoassay (the amount of analyte in the sample is inversely related to the amount of label measured in the indicator zone) and microarray. As a deviation from the description above it is also possible according to the novel concept to measure decrease of signal as in competitive immunoassay or multiple spots (array) at same time.

EXAMPLE

Suitability of the present invention for THC immunoassays has been demonstrated. The test setup is briefly presented below.

The lateral flow devices used comprised a meandering-channel chips of the type shown in principle in FIG. 1A and as a photograph in FIG. 3A. The test zone was situated closer to the injection zone and the reference zone close to the waste reservoir. The test zone was provided with antibody sensitive to THC-immunocomplex in serum. The control zone contained a non-specific antibody as negative control. Alexa Fluor 546 labeled anti-THC antibody was mixed with the sample to form THC-anti-THC immunocomplex.

The chips were provided with four serum samples with 0, 50, 100 and 250 ng/ml THC concentration. Images of chips with 0 and 250 ng/ml concentration are shown in FIGS. 5A and 5B.

Imaging was carried out using a test setup with a mobile phone, the setup corresponding to that schematically shown in FIGS. 2A-2C. Roithner 532 nm lasermodules were used to illuminate the sample and to excite the fluorophore. Chroma ZET405/473/532/640m was used to block undesired reflections of excitation light. An iPhone® 5S was used as the imaging device. FIG. 5 shows the absorption and emission spectra of Alexa fluor 546 and the filter spectrum of FF01-593/40.

Figure 4A:
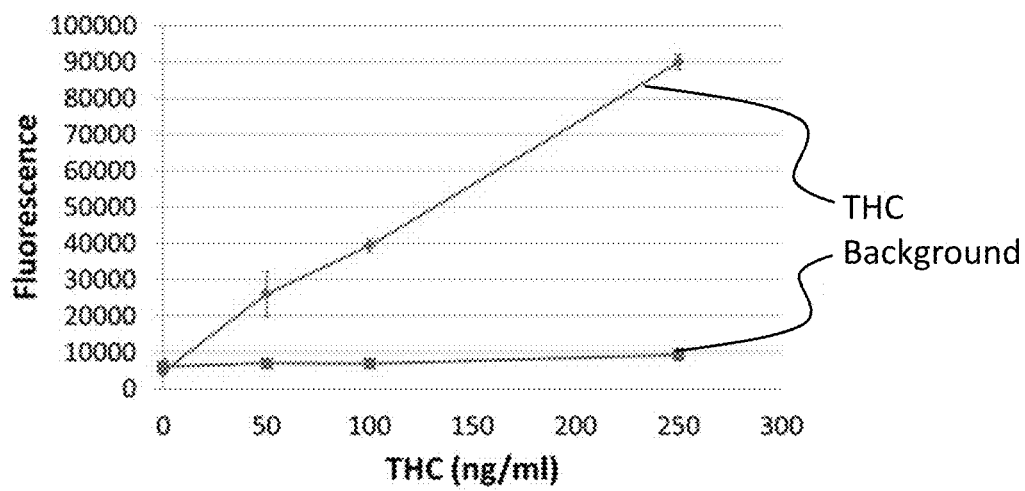
FIGS. 4A and 4B show measured fluorescence THC assay response signals using a commercial fluorometer and a mobile phone-aided lateral flow system according to the present invention, respectively.

A reference system was also used, comprising a commercial fluorometer. Results of the reference setup measurement are shown in FIG. 4A. It can be seen that the fluorescence signal measured increases roughly linearly as the THC concentration increases.

Figure 4B:
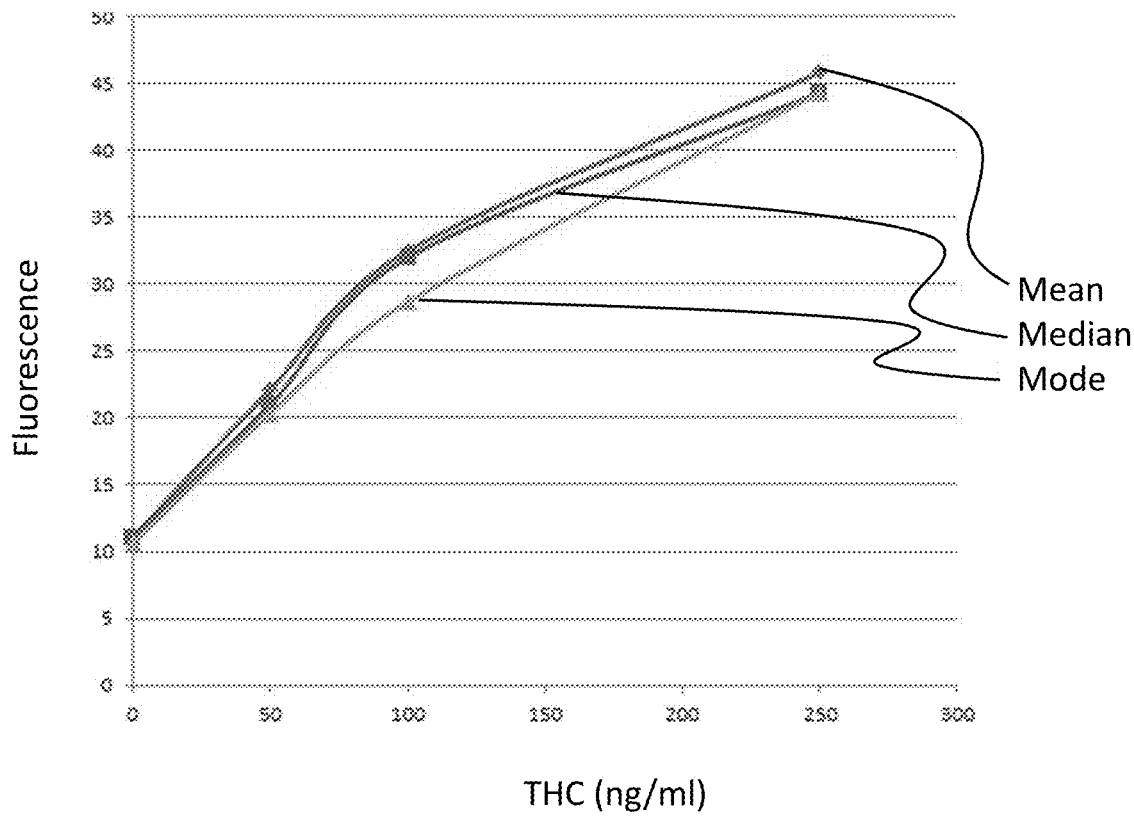

Results of the test setup measurement are shown in FIG. 4B. The graph comprises Mean, Median and Mode curves of THC concentration using steps 1-3 of the exemplary analysis algorithm described above.

FIG. 4C shows an image of a test chip with 0 ng/ml THC concentration and FIG. 4D with 250 ng/ml THC concentration. The difference of the optical response signal of the test zone can be clearly seen.

It can be seen, that the THC concentration can be well detected and the response signal of the test setup corresponds roughly to that of the reference setup. It can be concluded that the test measurement has been reliable and thus the curves of FIG. 4B could be used as reference curves for further experiments with unknown samples using steps 1 to 4 of the exemplary analysis algorithm described above.

It should be noted that the reference zone adjacent to the test zone is used to ascertain that the signal originates from the immunoreaction as opposed to being a reflection or another error signal. The reference zone therefore contained an antibody, which should not attract THC and thus represents a negative control.

It can be well assumed that the invention works as well in other immunoassays with suitable fluorescent antibodies.

LIST OF REFERENCE NUMERALS

| Number | Part |
|---|---|
| 10 | flow plate |
| 11 | support structure |
| 11A | bottom section |
| 11B | intermediate section |
| 11C | top section |
| 12 | injection zone |
| 13 | flow channel |
| 14A | first portion |
| 14B | second portion |
| 15 | turning portion |
| 15' | branching portion |
| 16 | reference zone |
| 19 | imaging area |
| 20 | flow plate |
| 21 | imaging panel |
| 22 | mobile phone |
| 23 | imaging optics |
| 24 | optical unit |
| 25 | lens of optical unit |
| 26 | light source |
| 97 | lens |
| 28 | camera |
| 29 | filter |
| 30 | flow plate |
| 32 | mobile phone |
| 34 | docking station |
| 35 | frame |
| 56 | indicator zone |

The invention claimed is:

1. A lateral flow device for an assay device for analyzing a fluid sample, the lateral flow device comprising:
   a support structure,
   a flow channel formed into the support structure, wherein the flow channel comprises a first indicator zone capable of facilitating an optically detectable response signal of the fluid sample interacting with an indicator substance,
   an injection zone in fluidic connection with the flow channel for introducing the fluid sample into the flow channel, and
   a second indicator zone capable of facilitating an optically detectable response signal of the fluid sample interacting with an indicator substance and arranged:
      parallel to the first indicator zone, wherein the first and second indicator zones are located side-by-side in a direction transverse to the direction of fluid flow in the flow channel, or
      to another flow channel formed into the support structure,
   wherein;
      the first and second indicator zones are arranged at least partly adjacent to each other so as to fit into an imaging area,
      the indicator zones fit into a circular imaging area having a diameter of 5 mm in a plane of the support structure,
      the injection zone comprises an indicator substance capable of providing an optical response signal upon interaction with a matrix of the fluid sample,
      at least one of the indicator zones comprises test substance capable of providing an optical response signal upon interaction with an analyte of the fluid sample,
      the first indicator zone is a test or reference zone and the second indicator zone is a reference or test zone, respectively, and wherein
      at least one of the indicator zones comprises a substance capable of providing a fluorescent optical response signal upon interaction with the fluid sample.

2. The lateral flow device according to claim 1, wherein the first and second indicator zones are arranged to the same flow channel and at least partly adjacent to each other at different portions of the flow channel.

3. The lateral flow device according to claim 1, wherein the flow channel is hollow.

4. The lateral flow device according to claim 3, wherein the hollow flow channel is free of a lateral flow matrix and dimensioned to provide a capillary flow of the fluid sample.

5. The lateral flow device according to claim 2, wherein the flow channel comprises a turning portion, whereby said portions are defined by different sides of the turning portion.

6. The lateral flow device according to claim 1, wherein the flow channel comprises a branching portion, whereby said portions are defined by different branches of the flow channel.

7. The lateral flow device according to claim 1, wherein the shortest distance between the indicator zones is less than 10 times the width of the flow channel.

8. The lateral flow device according to claim 1, wherein the lateral flow device contains at least two indicator zones comprising different test substances capable of providing optical response signals upon interaction with different analytes of the fluid sample.

9. The lateral flow device according to claim 8, wherein at least one of the indicator zones comprises a substance capable of providing a fluorescent optical response signal upon interaction with the fluid sample.

10. The lateral flow device according to claim 1, wherein the support structure is transparent on at least one side, at least in the region of the indicator zones, so as to allow optical imaging thereof during flow of the fluid sample.

11. The lateral flow device according to claim 1, wherein the support structure comprises a planar plate comprising a uniform bottom section, at least a partly transparent top section comprising said injection zone, and an intermediate section between the bottom and top section, the intermediate section being patterned to define the flow channel in the lateral dimension of the plate.

12. The lateral flow device according to claim 1, wherein the location of the indicator zones is marked thereon using visually detectable markers.

* * * * *